(12) United States Patent
Lading

(10) Patent No.: US 9,161,701 B2
(45) Date of Patent: *Oct. 20, 2015

(54) METHOD AND AN APPARATUS FOR DETERMINATION OF BLOOD PRESSURE

(71) Applicant: QUALCOMM Incorporated, San Diego, CA (US)

(72) Inventor: Lars Lading, Roskilde (DK)

(73) Assignee: QUALCOMM Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/202,062

(22) Filed: Mar. 10, 2014

(65) Prior Publication Data

US 2014/0187977 A1    Jul. 3, 2014

Related U.S. Application Data

(63) Continuation of application No. 11/993,612, filed as application No. PCT/DK2006/000378 on Jun. 27, 2006, now Pat. No. 8,690,785.

(30) Foreign Application Priority Data

Jun. 27, 2005 (DK) .................................. 2005 00953

(51) Int. Cl.
*A61B 5/021* (2006.01)
*A61B 5/00* (2006.01)

(52) U.S. Cl.
CPC ........... *A61B 5/02141* (2013.01); *A61B 5/0002* (2013.01); *A61B 5/021* (2013.01);
(Continued)

(58) Field of Classification Search
CPC ............ A61B 5/02141; A61B 5/7278; A61B 5/6832; A61B 5/02125; A61B 5/021; A61B 5/6833; A61B 5/0002; A61B 5/6824; A61B 2560/0219

USPC .................................. 600/490, 494, 488, 485
See application file for complete search history.

(56) References Cited

U.S. PATENT DOCUMENTS 4,269,193 A    5/1981    Eckerle
4,687,476 A    8/1987    Pailin
(Continued)

FOREIGN PATENT DOCUMENTS

EP    0319160    6/1989
FR    2700683    7/1994
(Continued)

OTHER PUBLICATIONS

Japanese Office Action dated Dec. 20, 2011.
(Continued)

*Primary Examiner* — Michael Kahelin
*Assistant Examiner* — Tho Tran
(74) *Attorney, Agent, or Firm* — The Marbury Law Group, PLLC

(57) ABSTRACT

A method and an apparatus for non-interfering blood pressure measurements, relates to an apparatus for continuously monitoring blood pressure for patients at home or at work. The apparatus includes an extra-corporal sensor for blood pressure determination with a flexible housing adapted to be attached to the body of a living being proximate to an artery, and an electronic circuit for wireless coupling to a remote transceiver in accordance with the blood pressure in the artery, the remote transceiver adapted for wireless coupling to the sensor for generation of a pressure signal in accordance with the blood pressure in the artery, and a processor connected to the remote transceiver for reception of the pressure signal and adapted to estimate systolic and diastolic pressure based on the signal.

22 Claims, 6 Drawing Sheets

(52) U.S. Cl.
CPC ........... *A61B5/02125* (2013.01); *A61B 5/6832* (2013.01); *A61B 5/6833* (2013.01); *A61B 5/7278* (2013.01); *A61B 5/6824* (2013.01); *A61B 2560/0219* (2013.01)

(56) References Cited

U.S. PATENT DOCUMENTS

| | | |
|---|---|---|
| 4,799,491 A | 1/1989 | Eckerle |
| 5,199,438 A | 4/1993 | Pearlman et al. |
| 5,441,968 A | 8/1995 | Brandstrom et al. |
| 5,647,369 A | 7/1997 | Petrucelli et al. |
| 6,015,386 A | 1/2000 | Kensey et al. |
| 6,015,387 A | 1/2000 | Schwartz et al. |
| 6,206,835 B1 | 3/2001 | Spillman, Jr. et al. |
| 6,375,620 B1 | 4/2002 | Oser et al. |
| 6,409,674 B1 | 6/2002 | Brockway et al. |
| 6,533,729 B1 | 3/2003 | Khair et al. |
| 6,554,773 B1 | 4/2003 | Nissilae et al. |
| 6,558,225 B1 | 5/2003 | Reh Kemper et al. |
| 7,935,061 B1 | 5/2011 | Breed et al. |
| 8,690,785 B2 | 4/2014 | Lading |
| 2002/0059081 A1 | 5/2002 | Yasuda et al. |
| 2002/0151816 A1 | 10/2002 | Rich et al. |
| 2003/0032993 A1 | 2/2003 | Mickle et al. |
| 2003/0060721 A1 | 3/2003 | Nakazawa et al. |
| 2004/0133092 A1 | 7/2004 | Kain |
| 2004/0193058 A1 | 9/2004 | Montegrunde et al. |
| 2005/0015014 A1 | 1/2005 | Fonseca et al. |
| 2005/0119833 A1 | 6/2005 | Nanikashvili |
| 2006/0103506 A1 | 5/2006 | Rodgers et al. |
| 2007/0060812 A1 | 3/2007 | Harel et al. |
| 2009/0054866 A1 | 2/2009 | Teisen-Simony et al. |

FOREIGN PATENT DOCUMENTS

| | | |
|---|---|---|
| JP | 2001275998 | 10/2001 |
| JP | 2004049579 | 2/2004 |
| JP | 2004121866 | 4/2004 |
| JP | 2004350786 | 12/2004 |

OTHER PUBLICATIONS

International Search Report and Written Opinion—PCT/DK2006/000378—ISA/EPO—Dec. 28, 2006.

METHOD AND AN APPARATUS FOR DETERMINATION OF BLOOD PRESSURE

CROSS-REFERENCE TO RELATED APPLICATIONS

This application is a continuation of application Ser. No. 11/993,612 filed on Apr. 2, 2008 issued as U.S. Pat. No. 8,690,785 on Apr. 8, 2014, which is the national phase application under 35 U.S.C. 371 of PCT International Application No. PCT/DK2006/000378 which has an international filing date of Jun. 27, 2006, and also claims priority under 35 U.S.C. 119 to Danish application PA 2005 00953 filed on Jun. 27, 2005, which applications are hereby incorporated by reference in their entirety for all purposes as if fully set forth herein.

FIELD OF THE INVENTION

The present invention relates to a method and an apparatus for non-interfering blood pressure measurements. In particular, the invention relates to an apparatus for continuously monitoring blood pressure for patients at home or at work.

BACKGROUND OF THE INVENTION

Blood pressure can be measured in a number of ways, such as invasive pressure sensor, oscillometric, auscultatory and tonometric. These methods will inevitably affect the state of the patient. It has been reported that a considerable number of measurements performed at the office of a medical doctor or at a hospital are affected by the situation and may be quite erroneous compared to what would have been measured if the patient had not been affected by the medical environment. The variations of the blood pressure in relation to the activity of the patient may provide very important information in relation to diagnosis. Existing methods do not provide non-interfering recording of blood pressure during sleep or during physical activity. Existing systems with a minimum interference do require either electrical wired power connection or an internal battery. These facts impose limitations on the applicability of the system and may have undesirable environmental effects.

In U.S. Pat. No. 6,558,335, a wrist-mounted device is disclosed. The device is based on a conventional MEMS pressure sensor, and a local power supply in the form of a battery is required.

SUMMARY OF THE INVENTION

It is an object of the present invention to provide an apparatus that is suitable for continuous monitoring of blood pressure of a living being under normal living conditions.

According to the invention, the above-mentioned and other objects are fulfilled by an apparatus for determination of blood pressure, comprising an extra-corporal sensor for blood pressure determination with a flexible housing adapted to be attached to the body of a living being proximate to an artery, and an electronic circuit for wireless coupling to a remote transceiver in accordance with the blood pressure in the artery. The remote transceiver couples wirelessly to the sensor for generation of a signal in accordance with the blood pressure in the artery, and a processor is connected to the remote transceiver for reception of the signal and is adapted to estimate systolic and diastolic pressure based on the signal.

Preferably, the sensor is an extra-corporal sensor, i.e. adapted for use outside the protecting membranes of the body of a living being. Preferably, the sensor is a passive sensor, i.e. a sensor that does not require wired connection to a power supply, e.g. a battery, in order to operate correctly. Preferably, the sensor relies on passive components, such as capacitors, inductors, resistors, etc., for its operation.

In an embodiment of the present invention, the sensor is an active sensor, i.e. a sensor that is connected to a power supply, such as a battery or an energy harvesting device, e.g. a sun cell, etc.

The operating principles of the apparatus according to the present invention are based on the fact that the diameter of an artery varies in response to variations of the blood pressure. Since the artery wall is flexible, the diameter of the artery expands with increasing blood pressure. The housing of the sensor according to the invention is also flexible so that the geometry of the housing changes when the housing is attached to the body of the living being proximate the artery. Electronic circuitry in the housing is adapted to sense geometric variations of the housing and provide an electronic parameter variation in response to the geometric variation. Further, the remote transceiver is adapted to wirelessly determine the electronic parameter variation.

The housing may be a flexible laminated polymer structure, and preferably, the electronic circuit is embedded in the structure whereby a small sensor is provided at a low cost.

The wireless coupling may be an inductive coupling, a capacitive coupling, an electromagnetic coupling, such as radio coupling or optical coupling, or a combination thereof, etc. The sensor circuit may include an antenna.

Preferably, the electronic circuit is a resonant circuit comprising an inductor and a capacitor.

In an embodiment of the present invention, the electronic circuit comprises a capacitor, and the capacitance of the capacitor may vary with the diameter of the artery when the housing is attached to the body proximate to the artery.

In an embodiment of the present invention, the electronic circuit comprises an inductor, and the inductance of the inductor may vary with the diameter of the artery when the housing is attached to the body proximate to the artery.

In yet another embodiment, the damping of the resonant circuit varies with the diameter of the artery when the housing is attached to the body proximate to the artery.

Preferably, a surface of the housing has a surface adhesive for attaching the housing to the body in a way similar to application of a plaster.

Alternatively, a strap may fasten the housing.

In an embodiment of the present invention, the electronic circuit comprises a first capacitor having a first plate and a second plate. The first plate and the second plate may be connected to a third plate and a fourth plate, respectively, for forming capacitive couplings between the sensor and the transceiver. The first plate and the second plate may be connected to an inductor for forming inductive coupling between the sensor and the transceiver.

The transceiver comprises a circuit for determination of variations of the properties of the sensor.

In one embodiment of the present invention, the transceiver comprises a fifth plate and a sixth plate for forming capacitive couplings with corresponding third and fourth plates of the sensor. The fifth plate and the third plate forms a capacitive coupling and the sixth plate and the fourth plate forms a capacitive coupling, when the transceiver is positioned close to the sensor, e.g. around 1 cm or less, preferably less than 1 mm. The transceiver may comprise an astable oscillator, such as a multi-vibrator, e.g. a bi-stable multi-vibrator. Variation in the capacitance of the first capacitor of the sensor may lead to variation in the duty-cycle and/or the frequency of one or more output signals from the oscillator.

A metal sheet, e.g. a flexible metal sheet, may form a plate of a capacitor.

In an embodiment of the present invention, the transceiver comprises a circuit for determination of the resonant frequency of the resonant circuit of the sensor. Preferably, the transceiver comprises a transmitting antenna coupled as part of a tank circuit, which in turn is coupled to an oscillator. A signal is generated which oscillates at a frequency determined by the tank circuit modified by the wireless coupling of the resonant circuit of the sensor. This signal is applied to a frequency discriminator, which in turn provides a signal from which the resonant frequency of the sensor circuit is determined.

In one embodiment, the transceiver transmits a signal scanning the frequency across a predetermined spectrum. The current passing through the transmitting antenna has a peak at the resonant frequency of the sensor. The resonant frequency and bandwidth are thus determined from this peak in the current.

Alternatively or in combination, the transceiver may transmit an excitation signal from the antenna. The wireless coupling to the sensor with the resonant circuit modifies the impedance of the transmitting antenna. The resonant frequency and bandwidth of the sensor circuit is determined based on the change of the impedance of the transmitting antenna.

In yet another embodiment, the transceiver transmits a broadband signal or a signal with multiple frequencies so that a current is induced in the resonant circuit of the wirelessly coupled sensor. The current oscillates at the resonant frequency of the resonant circuit. The transceiver further has a receiving antenna that receives the transmitted signal minus the energy that is absorbed by the sensor. Thus, the power spectrum of the received signal will exhibit a minimum at the resonant frequency of the sensor. The resonant frequency and bandwidth of the sensor circuit are determined from this notch in the power spectrum of the received signal.

Transmitting two frequencies on either side of the peak frequency of the resonant circuit will make it possible to obtain an s-curve response by estimating the difference in the return signals at the two frequencies.

The impedance characteristics of the sensor may be estimated from the estimated spectral response. This complex spectral response, which gives both amplitude and phase, can be obtained by a Fourier Transform procedure and compensating for the spectral distribution of the transmitted signal. The moments of the spectrum, which can give the total spectral power, the centre frequency, the spectral width and other spectral parameters, can be obtained from the derivatives of the correlation function corresponding to the spectrum. Estimates of the moments can be obtained by correlating different orders of temporal derivatives of the return signal.

The state of the sensor may also be detected with an impedance analyzer that can detect both the amplitude and phase characteristics of the sensor through a coupling device like a coil, a capacitor or an antenna.

The transceiver may be adapted to communicate, e.g. by wire or wirelessly, with a computer comprising a processor. The processor may be adapted to record a signal from the transceiver and perform the calculations for determination of pulse, systolic and diastolic blood pressure from the signal from the transceiver, temporal variations of these quantities as well as statistical properties, such as mean value, variance, correlation factors, etc., of these variations. Further, the computer may be adapted for displaying the calculated values and plotting values as a function of time. In a preferred embodiment, the transceiver communicates wirelessly with the computer, e.g. in accordance with the Bluetooth or the ZigBee standard, or any other suitable wireless protocol.

In an embodiment, the processor is located in the transceiver. The transceiver may further comprise a display for displaying determined values, e.g. the systolic and diastolic blood pressure and the pulse.

DETAILED DESCRIPTION OF PREFERRED EMBODIMENTS

Figure 1:
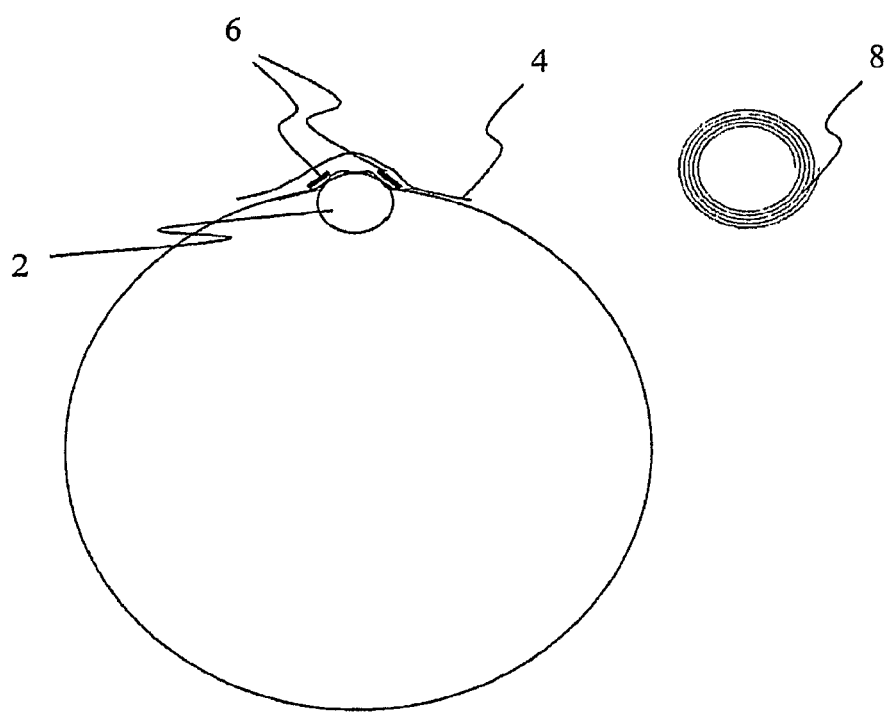
FIG. 1 schematically illustrates a cross-section of a sensor according to the present invention applied above an artery of a living being.

FIG. 1 schematically illustrates a cross-section of a sensor according to the present invention applied above an artery 2 of a living being. The sensor is supported by a flexible housing in the form of a flexible foil 4 that has an adhesive on its lower surface for attachment of the sensor to the skin surface immediately above the artery 2. The foil 4 supports mutually isolated metal sheets 6 forming a capacitor. The foil 4 is applied so that each of the metal sheets is positioned in close proximity to the artery 2. An inductor 8 is shown separately. The inductor 8 is printed into the foil 4. The capacitor and the inductor 8 are interconnected to form a resonant circuit and in the illustrated exemplary embodiment, the inductor value is fixed while the capacitor value varies with the diameter of the artery 2. An increased diameter of the artery 2 increases the distance between the metal sheets 6 decreasing the capacitor value.

In another embodiment, the inductor value varies with the diameter of the artery 2 while the capacitor value is fixed.

Figure 2:
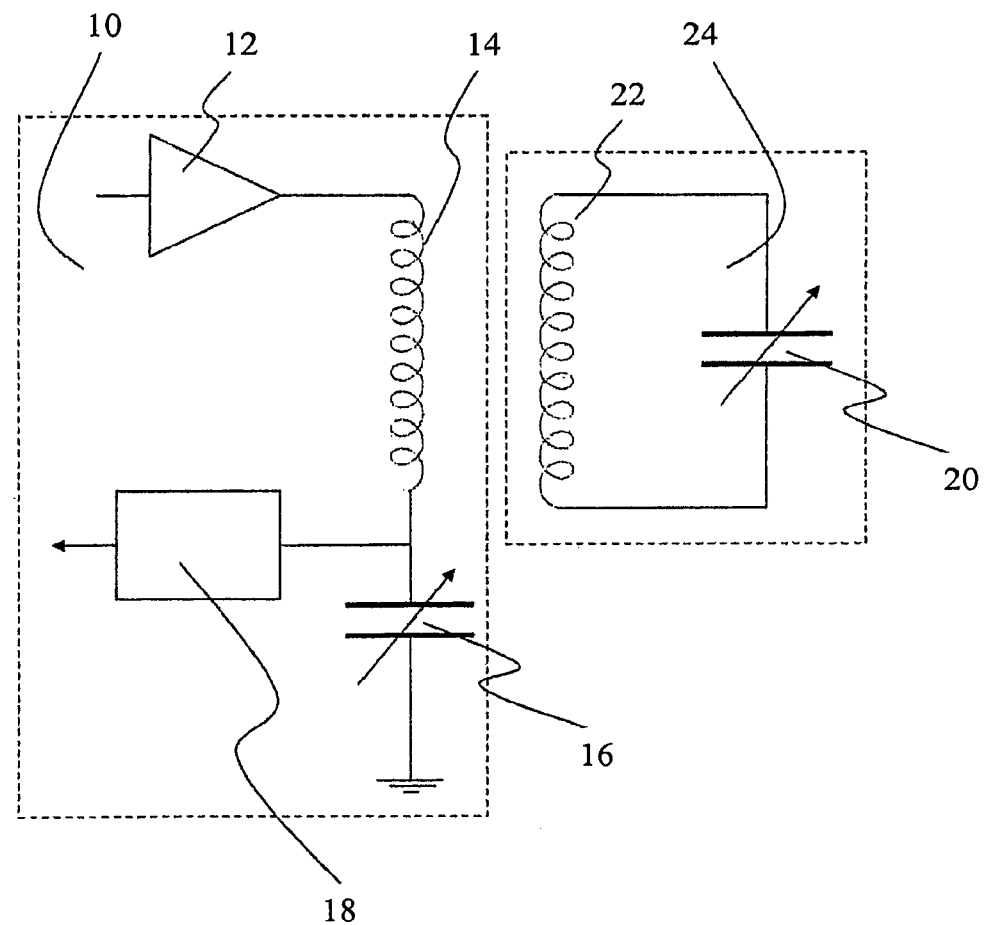
FIG. 2 is a blocked schematic of a sensor and a transceiver according to the present invention.

FIG. 2 is a blocked schematic of a sensor and a transceiver according to the present invention. The transceiver circuitry 10 comprises an amplifier 12, an inductor 14, a variable capacitor 16, and a frequency discriminator circuit 18. The inductor 14 and capacitor 16 forms a magnetically coupled resonant circuit together with the capacitor 20 and the inductor 22 of the sensor circuit 24. The resulting resonant frequency varies as a function of the value of capacitor 20 in the sensor circuit, which in turn varies in response to the blood pressure to be determined. The frequency discriminator circuit 18 detects the resulting resonance frequency and generates an electronic pressure signal with a value corresponding to the detected resonance frequency.

Figure 3:
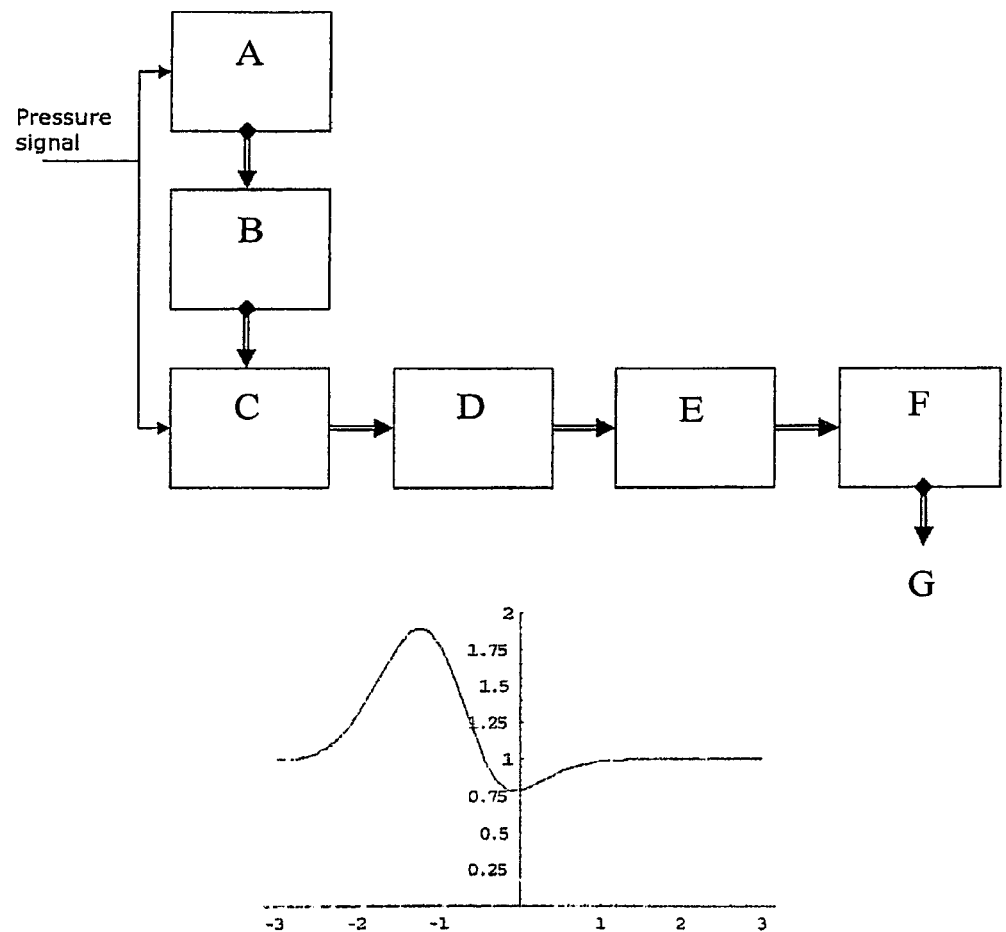
FIG. 3 is flowchart of an exemplary signal processing scheme according to the present invention, FIG. 4 schematically illustrates the various components of an embodiment of the present invention, FIG. 5 schematically illustrates a sensor and a transceiver according to the present invention, and FIG. 6 schematically illustrates an astable multi-vibrator comprised in a transceiver as illustrated in FIG. 5.

FIG. 3 is a flowchart of a preferred signal processing scheme according to the present invention. The pressure signal is determined at regular time intervals, and the determined values are fitted to an expected shape of the blood pressure as a function of time. The fitting is performed as a linear or non-linear least square fit. The fitting function is stretched to substantially match the temporal distance between consecutive heartbeats. The fitted curves are averaged over a period to be selected according to medical indication. For example, the fitted curves may be conditionally averaged over a period shorter than the characteristic time scale within which the blood pressure values may change. The conditional averaging is based on a good determination of the pulse. An averaged blood pressure curve is plotted at the lower part of FIG. 3. The averaging period is typically much larger than the time interval between consecutive pressure pulses. The maximum value and the minimum value of the averaged curve are determined for provision of the systolic and the diastolic blood pressure, respectively. Further, the average time difference between consecutive pulses is also determined for provision of the pulse. A calibration with a certified blood pressure measuring device is performed regularly.

In the illustrated embodiment, the signaling processing scheme thus comprises the steps:
A: Estimation of pulse spacing,
B: Reference pulse stretching,
C: Fitting,
D: Averaging,
E: Max. and Min. estimation, and
F: Weighting on the basis of a calibration.

The output G of the signal processing is estimates of systolic and diastolic pressure.

Figure 4:
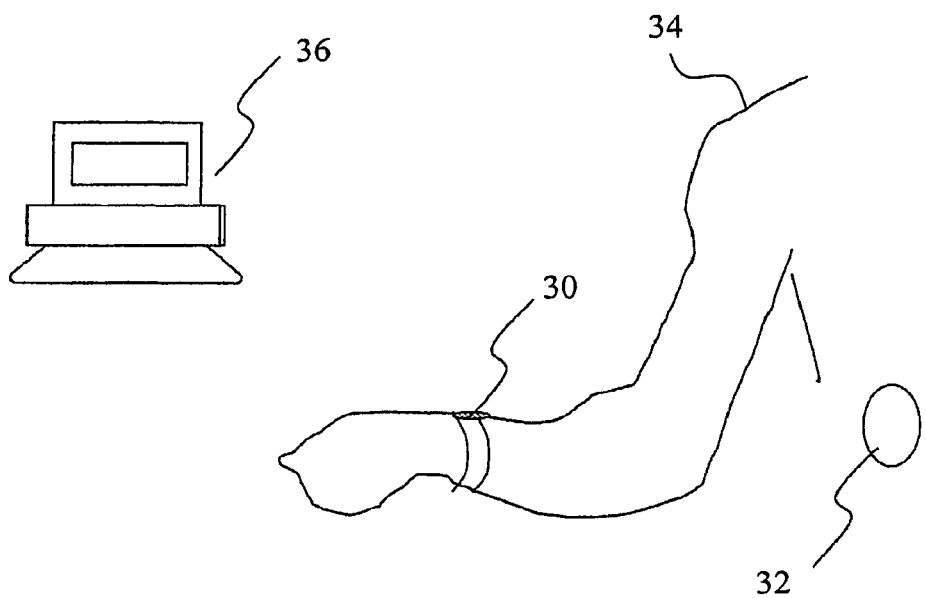

FIG. 4 schematically illustrates the various components of an embodiment of the present invention. The sensor 30 is typically mounted on the wrist of a patient. However, other positions may be selected as appropriate provided that an artery is close to the surface of the skin at the selected position. In the illustrated embodiment, the sensor 30 is a passive sensor that is fixed on the body above an artery. Preferably, the sensor has an adhesive surface for attaching the sensor to the body. The transceiver 32 is placed conveniently on the body of the patient 34 or adjacent the patient. The illustrated transceiver 32 communicates with a computer 36 with a processor that is adapted to record the pressure values and perform the calculations for determination of pulse, systolic and diastolic blood pressure. Further, the computer 36 is adapted for displaying the calculated values and plotting values as a function of time. In a preferred embodiment, the transceiver 32 communicates wirelessly with the computer, e.g. in accordance with the Bluetooth or the ZigBee standard.

In another embodiment, the processor is located in the transceiver. The transceiver may further comprise a display for displaying determined values, e.g. the systolic and diastolic blood pressure and the pulse.

Figure 5:
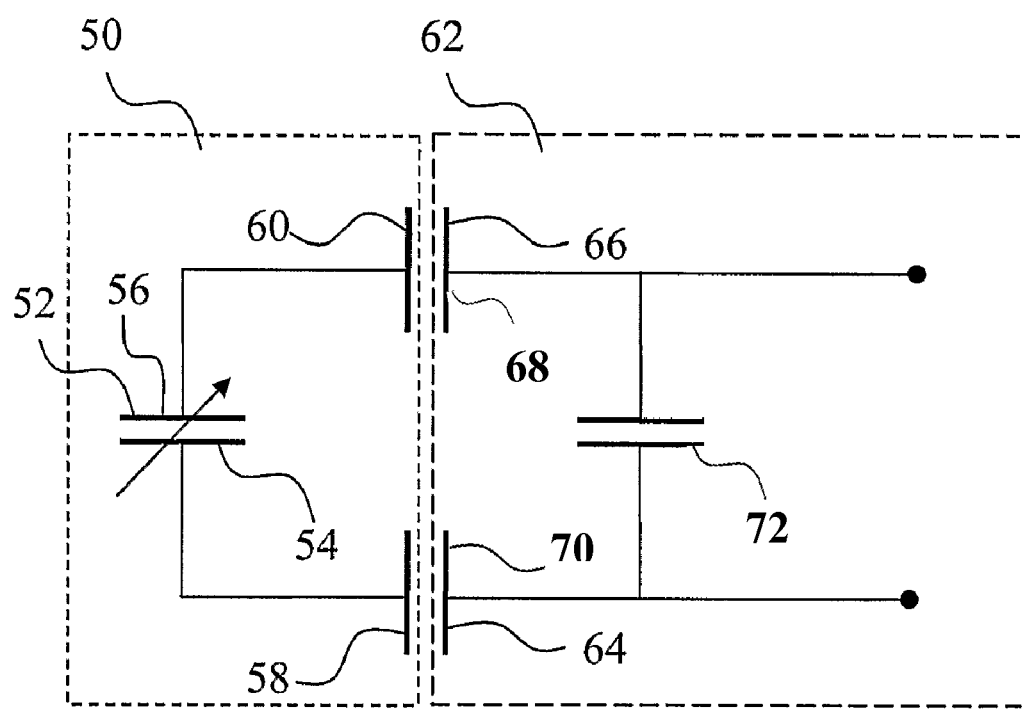

FIG. 5 is a blocked schematic of a sensor and a part of a transceiver according to the present invention illustrating a coupling between the sensor and the transceiver. The sensor 50 comprises a first capacitor 52 having two metal sheets forming a first plate 54 and a second plate 56, wherein the capacitance of the first capacitor 52 varies with the diameter of the artery when the housing is attached to the body proximate to the artery. The first plate 54 and the second plate 56 are connected to a third plate 58 and a fourth plate 60, respectively, for forming capacitive couplings between the sensor 50 and the transceiver 62. The transceiver 62 comprises a fifth plate 64 and a sixth plate 66 for forming capacitive couplings with corresponding third 58 and fourth 60 plates of the sensor. The capacitance of the second capacitor 68 and the third capacitor 70, respectively, is substantially constant during measurement. The second capacitor 68 and the third capacitor 70 may also be referred to as coupling capacitors. The transceiver may comprise a fourth capacitor 72. The transceiver 62 is adapted for measuring the variations in the first capacitor 52 whose capacitance varies as a function of time.

Figure 6:
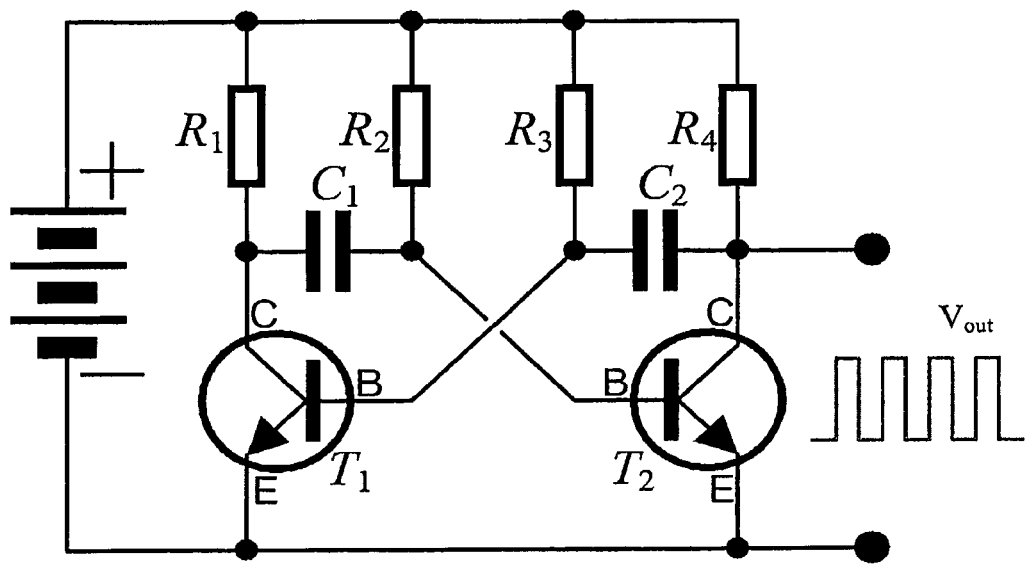

In an embodiment of the present invention, the transceiver 62 partly illustrated in FIG. 5 comprises an astable oscillator, which is schematically illustrated in FIG. 6. The capacitor $C_1$ indicates the varying capacitance of the circuit illustrated in FIG. 5. The transceiver may comprise a signal processing unit that is adapted to process the output signal $V_{out}$ from the oscillator. In an embodiment, the duty cycle of the output signal $V_{out}$ reflects the varying capacitance of the sensor, and the signal processing unit is adapted to determine the duty cycle of the output signal. Alternatively or in combination, the signal processing unit may be adapted to derive frequency information from the output signal $V_{out}$. The circuit of FIG. 5 may constitute or be a part of one of the capacitors $C_1$ and/or $C_2$.

The invention claimed is:

1. A blood pressure determination sensor comprising:
a flexible housing with a lower surface and a plurality of metal sheets comprising at least a first and a second mutually isolated metal sheets, wherein the flexible housing supports the first and the second mutually isolated metal sheets on the lower surface and comprises an attaching means such that when the flexible housing is attached to a body of a patient, proximate to an artery using the attaching means, the first and the second mutually isolated metal sheets form plates of a capacitor with at least the artery as a dielectric between the plates;
an inductor located in the flexible housing and electrically connected to the first and the second mutually isolated metal sheets such that the capacitor, formed when the flexible housing is attached to the body of the patient, and the inductor are interconnected to form a resonant circuit as an electronic sensor circuit, wherein a resonant frequency of the resonant circuit varies with a diameter of the artery in accordance with blood pressure;
a transceiver comprising a circuit, wirelessly coupled to the resonant circuit, that generates a pressure signal corresponding to variations of the resonant frequency of the resonant circuit; and
a computer comprising a processor configured to record the resonant frequency of the resonant circuit of the blood pressure determination sensor from the pressure signal and perform calculations for determination of the blood pressure of the patient using the resonant frequency of the resonant circuit.

2. The blood pressure determination sensor of claim 1, wherein the computer is coupled to the transceiver by wire.

3. The blood pressure determination sensor of claim 1, wherein the transceiver is coupled to the electronic sensor circuit by capacitive couplings for generation of the pressure signal in accordance with the blood pressure in the artery, wherein the first and the second mutually isolated metal sheets are electrically connected to a third metal sheet and a fourth metal sheet, respectively, for forming the capacitive couplings between the electronic sensor circuit and the transceiver.

4. The blood pressure determination sensor of claim 3, wherein the transceiver comprises a fifth metal sheet and a sixth metal sheet arranged to form the capacitive couplings to the third metal sheet and the fourth metal sheet of the electronic sensor circuit, wherein the fifth metal sheet and the third metal sheet is arranged to form a first capacitive coupling and the sixth metal sheet and the fourth metal sheet is arranged to form a second capacitive coupling.

5. The blood pressure determination sensor of claim 1, wherein the transceiver is coupled to the electronic sensor circuit by an inductive coupling for generation of the pressure signal in accordance with the blood pressure in the artery, the transceiver is coupled to the electronic sensor circuit via the inductor or via a further inductor coupled to the first and second metal sheets.

6. The blood pressure determination sensor of claim 1, wherein the transceiver is positioned with a distance to the electronic sensor circuit of less than 1 mm.

7. The blood pressure determination sensor of claim 1, wherein the transceiver comprises an astable oscillator.

8. The blood pressure determination sensor of claim 1, wherein the processor is connected to the transceiver for reception of the pressure signal and adapted to estimate systolic and diastolic pressure based on the pressure signal.

9. The blood pressure determination sensor of claim 1, wherein the flexible housing is constructed such that damping of the resonant circuit varies with the diameter of the artery when the flexible housing is attached to the body proximate to the artery.

10. A method for determining a blood pressure of a patient, the method comprises:
    providing a blood pressure determination sensor comprising a flexible housing with a lower surface, a plurality of metal sheets comprising at least a first and a second mutually isolated metal sheets supported on the lower surface, and an inductor located in the flexible housing and electrically connected to the first and the second mutually isolated metal sheets;
    attaching the blood pressure determination sensor to an exterior of a body of the patient, proximate to an artery, such that the first and the second mutually isolated metal sheets form plates of a capacitor with at least the artery as a dielectric between the plates, the capacitor and the inductor being interconnected to form a resonant circuit as an electronic circuit, wherein a resonant frequency of the resonant circuit varies with a diameter of the artery in accordance with blood pressure;
    generating a pressure signal corresponding to variations of the resonant frequency of the resonant circuit; and
    performing via a processor of a computer calculations for determination of the blood pressure of the patient using the resonant frequency of the resonant circuit.

11. The method of claim 10, further comprising attaching the blood pressure determination sensor using a strap to the exterior of the body of the patient.

12. The method of claim 10, wherein the flexible housing is a flexible foil having a lower surface with an adhesive thereon, wherein the method further comprises attaching the blood pressure determination sensor using the adhesive to the exterior of the body of the patient.

13. The method of claim 12, wherein the flexible foil supports the first and the second mutually isolated metal sheets on the lower surface.

14. The method of claim 10, wherein the method further comprises determining pulse, systolic and diastolic blood pressure from the pressure signal.

15. The method of claim 10, wherein the dielectric of said capacitor comprises tissue through which field lines of said capacitor extend when extending into the artery.

16. The method of claim 10, wherein variations of the blood pressure results in variations of the diameter of the artery and the method further comprises determining variations of a capacitance of the capacitor caused by the variations of the diameter of the artery, and determining the blood pressure based on the variations of the capacitance.

17. The method of claim 10, wherein variations of the blood pressure results in variations of the diameter of the artery and the method further comprises determining variations of an inductance of the inductor caused by the variations of the diameter of the artery, and determining the blood pressure based on the inductance of the inductor.

18. The method of claim 10, wherein the method comprises determining a pressure signal related to the blood pressure at regular time intervals by fitting an expected blood pressure function of time to the variations of the resonant frequency of the resonant circuit.

19. The method of claim 10, wherein the method further comprises attaching said blood pressure determination sensor to a wrist of the patient.

20. The method of claim 10, wherein damping of the resonant circuit varies with the diameter of the artery, the method comprises determining variations of the damping of the resonant circuit.

21. A blood pressure determination sensor comprising:
    a processor;
    a flexible housing having a lower surface configured to be attached to a body of a patient proximate to an artery; and
    a plurality of mutually isolated metal sheets comprising at least a first metal sheet and a second metal sheet electrically connected to an inductor;
    wherein the plurality of mutually isolated metal sheets and the inductor are arranged on the lower surface of the flexible housing such that, when the flexible housing is attached to the body of the patient proximate to the artery, the first metal sheet and the second metal sheet form plates of a capacitor having at least the artery as a dielectric therebetween and the inductor interconnects to the capacitor forming a resonant circuit as an electronic sensor circuit;
    wherein a resonant frequency of the resonant circuit varies with a diameter of the artery in accordance with blood pressure; and
    wherein the processor is configured to use the resonant frequency to calculate blood pressure.

22. A method for determining a blood pressure of a patient, the method comprises:
    obtaining a blood pressure determination sensor comprising a flexible housing having a lower surface attachable to an exterior of a body of the patient and a plurality of mutually isolated metal sheets comprising at least a first metal sheet and a second metal sheet electrically connected to an inductor, the plurality of mutually isolated metal sheets and the inductor are arranged on the lower surface of the flexible housing;
    attaching the flexible housing of the blood pressure determination sensor to the body of the patient proximate to an artery, wherein the first metal sheet and the second metal sheet form plates of a capacitor having at least the artery as a dielectric therebetween and the inductor interconnects to the capacitor forming a resonant circuit as an electronic sensor circuit;
    determining a resonant frequency of the resonant circuit that varies with a diameter of the artery in accordance with blood pressure; and
    determining via a processor of a computer the blood pressure of the patient using the resonant frequency of the resonant circuit.

* * * * *